United States Patent [19]
Tomes et al.

[11] Patent Number: 5,026,647
[45] Date of Patent: Jun. 25, 1991

[54] SELECTIVE MEDIUM FOR PROPIONIBACTERIUM GROWTH

[75] Inventors: Nancy J. Tomes, Cumming; Carol A. Henderick, Des Moines; Bonita A. Glatz, Ames, all of Iowa

[73] Assignee: Pioneer Hi-Bred International, Inc., Des Moines, Iowa

[21] Appl. No.: 518,493

[22] Filed: May 3, 1990

[51] Int. Cl.$^5$ .................... C12N 1/38; C12N 1/36; C12N 1/20; C12R 1/01
[52] U.S. Cl. .................... 435/244; 435/42; 435/245; 435/253.6
[58] Field of Search ............. 435/42, 244, 245, 253.6

[56] References Cited

U.S. PATENT DOCUMENTS

| | | | |
|---|---|---|---|
| 2,143,358 | 1/1939 | Walch et al. | 435/244 |
| 4,432,998 | 2/1984 | Peer | 435/245 |
| 4,476,224 | 10/1984 | Adler | 435/253.6 |
| 4,615,978 | 10/1986 | Sandine et al. | 435/253.6 |
| 4,732,855 | 3/1988 | Zeikus et al. | 435/244 |
| 4,766,076 | 8/1988 | Sandine et al. | 435/253.6 |
| 4,888,293 | 12/1989 | Hackl et al. | 435/245 |

FOREIGN PATENT DOCUMENTS 3202390  8/1988  Japan .................... 435/244

OTHER PUBLICATIONS

Liu et al., "Applied & Envir. Microbiol.", 9-1982, pp. 715-722, vol. 44, #3.
Hettinga et al., "Journal Food Tech.", 35:295-301, 358-372, 436-447, (1972).

Primary Examiner—Herbert J. Lilling
Attorney, Agent, or Firm—Zarley, McKee, Thomte, Voorhees & Sease

[57] ABSTRACT

A method and medium for selective growth of Propionibacterium from mixed culture samples is disclosed. The medium comprises a lactic acid source as its primary energy or nutrient source and in combination therewith a small but effective amount of a heavy metal salt to which Propionibacterium is resistant, selected from a group of water-soluble cadmium and arsenic salts.

14 Claims, No Drawings

SELECTIVE MEDIUM FOR PROPIONIBACTERIUM GROWTH

BACKGROUND OF THE INVENTION

1. Field the Invention

This invention is related to a method and medium for selective growth of propionibacteria from mixed culture samples.

2. Brief Description of the Background Art

The use of silage additives has become a widely accepted practice throughout much of the agricultural world. In order to understand how silage additives react with silage, it may be helpful to first review the basic biochemical and microbiological changes that occur during the ensiling process. Immediately upon chopping of, for example, corn, aerobic respiration starts. During this early phase, soluble carbohydrates in the plant tissue are oxidized and converted to carbon dioxide and water. This process will continue until either the oxygen level is depleted or the water-soluble carbohydrates are exhausted. Under ideal conditions, with adequate packing and sealing of the ensiled material, respiration lasts only a few hours. The growth of microorganisms during this period is limited to those that are tolerant to oxygen which includes aerobic bacteria, yeast and molds. These organisms are generally recognized as being negative to the system as they metabolize sugar to carbon dioxide, heat, and water.

Recently it has become known that bacterial inoculants help preserve silage, including both grass silage and corn silage. For example, inoculation with lactic acid bacteria during the fermentation phase can be beneficial to the fermentation process, see for example U.S. Pat. No. 4,842,871 of Hill issued June 27, 1989, as well as the literature references cited therein. For high-moisture corn stability, this increase is probably due to the inoculant enhancing the rate of anaerobic fermentation and pH decrease. This is beneficial because oxidative losses caused by aerobic pH-sensitive microflora in the initial stages are thus avoided. In other silages such as whole corn plant, alfalfa, etc. the inoculant can also have beneficial effects on the digestibility of the silages by causing an increase in the availability of the fiber.

A co-pending and commonly assigned application relates to a bacterial inoculant for silage preservation which aids in stability in the second part of the process that occurs when a silo is opened to the air. This co-pending application, Ser. No. 431,883, Tomes, filed Nov. 6, 1989, the disclosure of which is incorporated herein by reference, in its broad aspects relates to treating silage with a preserving effective amount of the microorganism *Propionibacterium jensenii*, or the genetic equivalent. As a result, the metabolic products of the propionibacteria aid in assuring a stable product during their aerobic phase, when the silo is open.

It can therefore be seen that there is a continuing need for selective growth of species of Propionibacterium and particularly *Propionibacterium jensenii* to the exclusion of other species in mixed culture samples, so that Propionibacterium can be isolated for uses peculiar to Propionibacterium, such as use in the invention of the incorporated by reference application.

The primary objective of the present invention therefore is to fulfill the need for a medium which allows selective growth of Propionibacterium from mixed culture samples to the exclusion of other bacteria, particularly Lactobacillus.

Another objective of the present invention is to provide a medium and a method of use of the medium which allows not only growth of Propionibacterium to the selective exclusion of others like Lactobacillus, but also a medium which under proper conditions and selectivity of added agents allows strain selection within the genera of Propionibacterium to allow certain strains of Propionibacterium to grow to the exclusion of others.

A yet further objective of the present invention is to provide a medium composition useful in the methods described herein.

The method and manner of accomplishing each of the objectives of the invention as well as perhaps others will become apparent from the detailed description of the invention which follows hereinafter.

SUMMARY OF THE INVENTION

In the present invention, propionibacteria are selectively grown from mixed culture samples. This is accomplished by adding to a mixed culture sample a medium which contains lactate as its primary energy source and adding to the medium a small but effective amount of a heavy metal salt to which Propionibacterium is resistant, selected from the group of water soluble cadmium salts and water soluble arsenic salts. As a result, other bacteria in the mixed culture sample, such as Lactobacillus bacteria do not grow because they do not have the resistance to either water soluble cadmium salts or water soluble arsenic salts that is exhibited by Propionibacterium. In one preferred embodiment, the heavy metal salt is an arsenic salt and it is used in combination with an antibiotic which allows the medium to be strain selective within the genus of Propionibacterium to allow some strains of Propionibacterium to grow to the exclusion of other strains.

DETAILED DESCRIPTION OF THE INVENTION

In the incorporated by reference application of Tomes, Ser. No. 431,883, silage is treated with a preserving effective amount of a species of propionibacteria, particularly *P. jensenii* and most particularly strains P9 and PFargo, having ATCC numbers 53961 and 53962, respectively. In accordance with this invention, both P9 and PFargo can be selectively grown from mixed culture samples.

One approach to selectively recover a unique microflora in the presence of other microflora is to use a unique energy source that the competing microflora are unable to use. For example, if the population of competing microflora is 100× higher than the propionibacteria, counts on a nonselective medium that recovers both the propionibacteria and the competing microflora would not reflect the actual populations of each. In practice, it is usually sufficient to inhibit the competing microflora on selective media by a factor of 1000.

In one early report by Lui and Moon, interaction between *Lactobacillus acidophilus* and *Propionibacterium shermani*, Appl. Environ. Microbiol. 44:715-722 (1982), to adjust the medium that contained lactic acid as a major energy source was adjusted to recover propionibacteria from mixed cultures of *Lactobacillus acidophilus* and Propionibacterium. While this was useful because *L. acidophilus* did not utilize lactic acid anaerobically and thus the only bacteria recovered were propionibacteria, such proved not useful in the case of Propionibacterium in mixed cultures that contained other *L. Plantarum*. In sum, the composition of Lui and Moon was not sufficiently inhibitory to the natural flora of fermented plant material in order to provide selective inhibition in general which allowed Propionibacterium to grow, while simultaneously inhibiting others such as lactic acid bacteria present in fermented plant materials.

Therefore it was necessary to find a new medium which could be successfully used with other samples of populations that contained a variety of competing microflora.

In accordance with the present invention, it has been discovered that selective growth of Propionibacterium can be achieved in conventional lactate medium when there is added to the medium a small, but inhibition effective, amount of a heavy metal salt to which Propionibacterium is resistant which is either a water-soluble cadmium salt or a water-soluble arsenic salt. While it may be conceivable that other water-soluble heavy metal salts could also be used, to date, successes have only been achieved with cadmium salts and arsenic salts. The preferred water-soluble cadmium salt is cadmium chloride. The preferred water-soluble arsenic salts are arsenates.

The dosage amount used can vary, depending upon the medium, but generally will range in concentration, based upon concentration of the entire medium, of from about 0.1 mM to about 5.0 mM of the medium. Preferably, where the heavy metal salt is cadmium, the concentration is within the range of 0.1 mM to about 0.5 mM. Correspondingly, where the heavy metal salt is an arsenic salt, the concentration can vary over a wider range and can generally be from about 0.2 mM to about 5.0 mM.

It has been found that when heavy metal salts are dosed into the medium within the range herein specified, it makes the conventional lactate medium Propionibacterium selective.

This phenomena is somewhat surprising, since it has been known and reported that many Propionibacterium strains are not resistant to heavy metals, see for example Hettinga, D. H. and G. W. Reinbold. J. Food Technol. 35:295–301, 358–372, 436–447 (1972).

A source of lactate medium which can be useful for the present invention is not critical, and any conventional medium which contains a lactic acid energy source can be useful. For example, one satisfactory medium is reported in the following Table 1.

TABLE 1

| Components | Specific Lactate Medium | General Ranges |
|---|---|---|
| Yeast Extract | 10 g | 5 to 15 |
| Sodium Lactate 60% Syrup | 17.5 ml | 5 to 25 |
| $K_2HPO_4$ | .25 g | .1 to .4 |
| Agar | 15 g | 5 to 20 |
| Deionized Distilled Water | 1000 ml | 1000 ml |

The conditions under which the culture is grown are conventional and need not be recited herein. Generally a mixed culture containing the medium is held under controlled temperature and atmospheric conditions of 28° C. anaerobic environment for 5–7 days, a time sufficient for the bacteria to propagate and form colonies.

The following examples illustrate but do not necessarily limit the invention.

In the initial stages of the experimentation, results were obtained with other than arsenic and cadmium. In particular copper, tellurite and phenyl mercuric chloride were also used. The results of initial screening with those are shown in Table 2.

TABLE 2

The Effect of Various Inhibitory Compounds On the Growth of Pure Broth Cultures of Propionibacteria and Lactobacilli

| | Strain | | |
|---|---|---|---|
| Heavy Metal | *Lactobacillus sp.* | Prop. 8 | Prop. 9 |
| $AsO_2$ (0.01 mMolar) | + | ++ | ++ |
| $AsO_4$ (0.05 mMolar) | + | ++ | ++ |
| $CdCl_2$ (1 mMolar) | 0 | 0 | ++ |
| $CuCl_2$ (.1 mMolar) | ++ | + | ++ |
| Phenyl Mercuric Chloride (20 uMolar) | 0 | 0 | 0 |
| $K_2TeO_3$ | ++ | + | + |
| Lactate media Control | ++ | ++ | ++ |

It can be seen that these initial screening results suggest that the use of heavy metals had potential as selective agents, particularly arsenic and cadmium salts.

Follow-up test revealed that the resistance to arsenic is widespread in propionibacteria and that it is useful as a generally selective agent in a medium. The resistance to cadmium is not nearly as general in nature. However, some strains are much more resistant to cadmium than other strains within the same species. Thus, it is likely that this characteristic can be used for selective recovering of a unique strain of interest.

The following Table 3 shows the effect of cadmium or arsenic in lactate medium on growth of classical strains of Propionibacterium.

TABLE 3

THE EFFECT OF Cd OR $AsO_4$ IN LACTATE MEDIUM ON GROWTH OF CLASSICAL STRAINS OF PROPIONIBACTERIUM SP.

| | | CORN MEAL AGAR 1% GLUCOSE | | | |
|---|---|---|---|---|---|
| | STRAIN | PLATE 1 | PLATE 2 | 0.25 mM $CdCl_2$ | 1.0 MM $Na_2HAsO_4$ |
| $P_1$ | *P. thoenii* | ++ | ++ | ++ | ++ |
| $P_2$ | *P. jensenii* | ++ | ++ | − | ++ |
| $P_4$ | *P. thoenii* | ++ | ++ | − | ++ |
| $P_5$ | *P. acidipropionic* | ++ | ++ | − | ++ |
| $P_6$ | *P. thoenii* | ++ | ++ | ++ | ++ |
| $P_7$ | *P. thoenii* | ++ | ++ | − | + |
| $P_{10}$ | *P. jensenii* | ++ | ++ | − | ++ |
| $P_{11}$ | *P. thoenii* | ++ | ++ | ++ | ++ |
| $P_{12}$ | *P. thoenii* | ++ | ++ | ++ | ++ |
| $P_{13}$ | *P. thoenii* | ++ | ++ | ++ | + |
| $P_{16}$ | *P. thoenii* | ++ | ++ | ++ | ++ |

TABLE 3-continued

THE EFFECT OF Cd OR AsO4 IN LACTATE MEDIUM ON GROWTH OF CLASSICAL STRAINS OF PROPIONIBACTERIUM SP.

| STRAIN | | CORN MEAL AGAR 1% GLUCOSE | | 0.25 mM CdCl$_2$ | 1.0 MMNa$_2$$_H$AsO$_4$ |
|---|---|---|---|---|---|
| | | PLATE 1 | PLATE 2 | | |
| P$_{17}$ | P. jensenii | ++ | ++ | − | ++ |
| P$_{18}$ | P. freudenreichii | ++ | ++ | ++ | ++ |
| P$_{25}$ | P. jensenii | ++ | ++ | − | ++ |
| P$_{26}$ | P. jensenii | ++ | ++ | − | + |
| P$_{28}$ | Propionibacterium sp | ++ | ++ | − | + |
| P$_{29}$ | Propionibacterium sp | ++ | ++ | − | ++ |
| P$_{31}$ | P. freudenreichii | ++ | ++ | − | + |
| P$_{32}$ | P. freudenreichii | + | + | − | ++ |
| P$_{98}$ | P. freudenreichii | ++ | ++ | ++ | ++ |
| | P. jensenii fargo | ++ | ++ | ++ | ++ |
| | P. freudenreichii | ++ | ++ | ++ | ++ |
| 6207 | P. acidipropionici | ++ | ++ | ++ | + |

Previous experimental attempts to use antibiotics as potential selective agents had failed. Thus it was somewhat surprising that tests showed that the combination of arsenic salts and Netilmicin would work to selectively screen cultures to allow further selection within the genus of Propionibacterium to allow some strains to grow to the exclusion of others.

The following Table 4 reports results of tests using the antibiotic Netilmicin in combination with arsenic. Where this combination is used, the amount of Netilmicin should be within the range of from 10 micrograms to 100 micrograms per ml of medium.

TABLE 4

The effect of using mixtures of Netilmicin and arsenate in lactate agar medium on the growth (expressed as log colony forming units/ml culture broth) of selected strains of propionibacteria and lactobacilli

| Strain | lactate control | 30 ug NET 1.0 mMAsO$_4$= | 75 ug NET 1.0 mMAsO$_4$= | 30 ug NET 5.0 mMAsO$_4$= |
|---|---|---|---|---|
| 1186 | 8.39 | 8.12 | 7.90 | <4.00 |
| Prop 8 | 8.33 | 8.34 | 8.36 | 8.34 |
| Prop 9 | 8.06 | 7.98 | 7.75 | <4.00 |
| Lacto 1 | 7.49 | <4.00 | <4.00 | <4.00 |
| Lacto 2 | 7.94 | <4.00 | <4.00 | <4.00 |

It can be seen from the above table that the mixture of Netilmicin and arsenic was effective in inhibiting to all the lactobacilli tested but not the Propionibacterium, strain 8. The results and recovery from pure broth cultures were confirmed with tests on actual fermented grain samples, as shown in the next table of Examples, Table 5.

In the use of grain samples, they were obtained in the following manner. Powdered bacterial inocula were received in sufficient quantities to treat 250 lbs. The grain was divided into piles of 250 lbs. for treatment. Inocula were mixed vigorously in 200 ml of distilled water and hand pump spray bottles were used. One milliliter from each spray bottle was withdrawn and added to 9 ml of H$_2$O/Tween/PO$_4$ blank.

The inoculum was serially diluted in H$_2$O/Tween/PO$_4$ and 0.1 ml spread-plated on an appropriate medium, with the medium incubated at temperatures of 28° C. anaerobically for 7-10 days.

The remainder of the inoculum in the spray bottle was applied to individual grain piles. Twenty-two grams of grain from each pile were weighed and diluted 1:10 in H$_2$O/Tween/PO$_4$ blanks. The samples were blended for one minute, serially diluted in H$_2$O/Tween/PO$_4$ and 0.1 ml spread-plated on appropriate media and incubated.

Table 5 shows the recovery of pure cultures of strains of propionibacteria, lactic acid bacteria and high-moisture grain isolates on modified lactate medium with selective agents.

TABLE 5

The % Recovery of Propionibacterium Strains P-8 and P-9 From Fermented Grain In On Farm Trials

| MEDIUM | % RECOVERY | | |
|---|---|---|---|
| Lactate Medium + | P-8 | P-9 | P-Fargo |
| a. 30 mg Netilmicin + 1 mM Na$_2$HAsO$_4$ | 49 | 55 | <1% |
| b. 75 mg Netilmicin + 1 mM Na$_2$HAsO$_4$ | 40 | 35 | <1% |
| c. 30 mg Netilmicin + 5 mM Na$_2$HAsO$_4$ | 43 | 0 | <1% |
| d. + .1 mM CdCl$_2$ | ND | 169 | 85 |
| e. + .15 mM CdCl$_2$ | ND | 133 | 70 |
| f. + .25 mM CdCl$_2$ | ND | 101 | ND |

From the above experiments as summarized in the tables, 1-5, it can be seen that the use of heavy metal salts, particularly cadmium and an arsenate in a medium containing lactate acid as the primary energy source, is effective in eliminating many contaminants when isolating propionibacteria from natural environments. The selectivity of the medium can be increased by adding antibiotics, particularly Netilmicin (for populations of the propionibacteria of interest). When the populations of propionibacteria and others are approximately the same, the cadmium is equally satisfactory. The approach of the combination of the arsenate and the antibiotic can be used when a specific strain of propionibacteria is to be recovered to the exclusion of another.

Therefore, it can be seen that the invention accomplishes at least all of its stated objectives.

What is claimed is:

1. A method of selective growth of propionibacteria from culture samples containing several different genus and species of bacteria, comprising:

adding to a mixed culture sample containing propionibacteria a medium containing lactate as its primary energy source;

adding to said medium and culture sample a small but effective amount of a heavy metal salt to which *Propionibacterium Jensenii* is resistant, selected from the group of water-soluble cadmium salts and water-soluble arsenic salts; and allowing the culture to grow whereby propionibacteria selectively increase to the exclusion of other bacteria which are less resistant to the added heavy metal salts.

2. The process of claim 1 wherein the water-soluble heavy metal salts are cadmium salts.

3. The process of claim 2 wherein the water-soluble heavy metal salt is cadmium chloride.

4. The process of claim 1 wherein the water-soluble heavy metal salts are arsenic salts.

5. The process of claim 4 wherein the water-soluble heavy metal is an arsenate salt.

6. The process of claim 4 wherein the medium also has added to it an antibiotic which in combination with the arsenate is strain-selective within the genus Propionibacterium to allow *Propionibacterium jensenii* strains to grow to the selective exclusion of others.

7. The process of claim 6 wherein the antibiotic is Netilmicin.

8. The process of claim 1 wherein the added dose level of the water-soluble heavy metal salt is at a concentration of from about 0.1 mM to about 5.0 mM of the medium.

9. The process of claim 8 wherein the water-soluble heavy metal salt is cadmium chloride and the concentration is from 0.1 mM to about 0.5 mM.

10. The process of claim 8 wherein the water-soluble heavy metal salt is an arsenic salt and the concentration is from about 0.1 mM to about 5.0 mM.

11. A method of selective growth of *Propionibacterium jensenii* from a culture sample containing both Lactobacillus and Propionibacteria, said method comprising:

adding to said culture a small but *Propionibacterium jensenii* selective amount of a water-soluble heavy metal ion source selected from the group consisting of water-soluble salts of cadmium and arsenic.

12. The method of claim 11 wherein the heavy metal ion source is a water-soluble salt of arsenic.

13. The method of claim 12 wherein the water-soluble salt of arsenic is added along with addition of an antibiotic which is combination with the arsenic salt is species selective within the genus of Propionibacterium to allow *Propionibacterium jensenii* to grow to the selective exclusion of others.

14. The method of claim 13 wherein the antibiotic is Netilmicin.

* * * * *